United States Patent [19]

Sato et al.

[11] Patent Number: 5,446,213

[45] Date of Patent: Aug. 29, 1995

[54] DIMERIZATION METHOD OF LOWER OLEFINS AND ALCOHOL PRODUCTION WITH DIMERIZED PRODUCTS

[75] Inventors: Keiichi Sato, Tokyo; Yuuji Kawaragi; Yasuko Higashino, both of Yokohama, all of Japan

[73] Assignee: Mitsubishi Kasei Corporation, Tokyo, Japan

[21] Appl. No.: 244,212

[22] PCT Filed: Oct. 5, 1993

[86] PCT No.: PCT/JP93/01425

§ 371 Date: Jun. 3, 1994

§ 102(e) Date: Jun. 3, 1994

[30] Foreign Application Priority Data

Jun. 10, 1992 [JP] Japan .................................. 4-267570

[51] Int. Cl.$^6$ .................. C07C 29/141; C07C 31/125; C07C 11/02; C07C 2/30
[52] U.S. Cl. ..................... 568/883; 524/216; 560/76; 585/513
[58] Field of Search .................. 568/883; 585/513

[56] References Cited

U.S. PATENT DOCUMENTS

| | | | |
|---|---|---|---|
| 2,625,527 | 1/1953 | Smith et al. | 568/883 |
| 2,728,798 | 12/1955 | Russum et al. | 568/883 |
| 2,792,417 | 5/1957 | Dean | 568/883 |
| 3,255,259 | 6/1966 | Mertzweiller et al. | 568/883 |
| 3,459,825 | 8/1969 | Eberhardt et al. | |
| 3,467,726 | 9/1969 | Griffin, Jr. | |
| 3,513,218 | 5/1970 | Faltings et al. | |
| 3,636,034 | 1/1972 | Ohsumi et al. | 568/883 |
| 3,709,953 | 1/1973 | Bergen et al. | |
| 4,155,946 | 5/1979 | Sato et al. | |
| 4,476,341 | 10/1984 | Mathys | |
| 5,196,624 | 3/1993 | Threlkel et al. | |

FOREIGN PATENT DOCUMENTS 0569032 11/1993 European Pat. Off. .
46-34007 10/1971 Japan .
57-167932 10/1982 Japan .
57-169433 10/1982 Japan .
61-15849 1/1986 Japan .
789777 1/1958 United Kingdom .

*Primary Examiner*—Joseph E. Evans
*Attorney, Agent, or Firm*—Oblon, Spivak, McClelland, Maier, & Neustadt

[57] ABSTRACT

The present invention is directed to a method of dimerizing lower olefins which comprises dimerizing a lower olefins in the presence of a catalyst, wherein the catalyst used comprises a nickel compound, an organic aluminum compound, and a phosphite compound having the general formula (I):

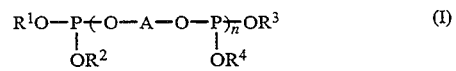

wherein $R^1$, $R^2$, $R^3$, and $R^4$ are phenyl groups optionally substituted by substituents and may be different from each other, at least two of $R^1$, $R^2$, $R^3$, and $R^4$ have a hydrocarbon group as a substituent in the ortho position; A is a divalent aliphatic, alicyclic or aromatic hydrocarbon group which optionally has a substituent; and n is 0 or 1. The present invention is also directed a method of producing alcohol by means of hydroformylating and hydrogenating the newly formed olefins obtained through the said dimerization method of the lower olefins. In the dimerization method of the lower olefins according to the present invention, it is possible to produce in an economic manner olefinic mixtures which are high in activity and low in degree of branching. In addition, the alcohols produced with the said olefins show totally superior performance as the raw material for plasticizers, which are thus valuable in industrial applications.

18 Claims, No Drawings

# DIMERIZATION METHOD OF LOWER OLEFINS AND ALCOHOL PRODUCTION WITH DIMERIZED PRODUCTS

TECHNICAL FIELD

This invention relates to a method of dimerizing lower olefins such as ethylene, propylene, and butene using a specific catalyst and to a method of producing alcohols with the dimerized products.

The dimerized products of olefins produced through dimerization method according to the present invention may be hydroformylated by reaction with carbon monoxide and hydrogen in the presence of an VIII metal catalyst such as a rhodium catalyst. The resultant aldehydes may be hydrogenated to alcohols. Reaction of the said alcohols with carboxylic acids such as phthalic acid results in the formation of esters. These esters are of great industrial importance because of their application as plasticizers for synthetic resins.

BACKGROUND ART

Many investigations have been made on catalytic systems that permit uniform dimerization of lower monoolefins such as ethylene, propylene, and butene. As the catalysts, Ziegler-type catalysts having transition metals as central catalyst component are usually superior in dimer selectivity of the lower monoolefins. In particular, satisfactory results have been obtained in dimerization activity and selectivity with a catalyst obtained from a mixture of a nickel compound and organic aluminum halide.

Investigations have also been made on catalytic systems containing organic phosphorus compounds as third additives to the above mentioned catalytic component. It is known that these additives affect on catalytic activity and product selectivity. As these catalytic system containing the organic phosphorus compounds, ① Japanese Patent Publication No. 46-34007 discloses a catalytic system comprising π-allyl-type nickel complex, an organic aluminum halide and an organic phosphine. ② Japanese Patent Publication Nos. 48-30241 and 50-30041 disclose catalytic systems comprising organic phosphine complexes of nickel represented by $(R_4P)^+(R_3PNiX_3)^-$ and $NiX'_2(PR'_3)_2$, respectively, where R represents hydrocarbyl group or hydrogen, X and X' each represents chlorine, bromine or iodine, and R' represents alkyl group. In addition, ③ Japanese unexamined Patent Publication No. 57-169433 discloses a catalytic system where halogenated phenol and water are added as fourth additives to a nickel compound, alkylaluminum and a trivalent phosphorus compound. It is disclosed to use, as the trivalent phosphorus compound in this case, trivalent organic phosphite compounds such as triethyl phosphite, tri-n-octyl phosphite, and triphenyl phosphite other than the above mentioned organic phosphine.

A large volume of $C_4$ fraction are obtained during thermal cracking of naphtha or catalytic cracking of heavy oils. n-butenes extracted and separated from the fraction may be dimerized to improve octene yields. ④ Japanese Patent Publication 3-42249 discloses an approach to improve the octene yields with a catalytic system comprising a nickel compound selected from the group consisting of nickel salts of higher mono- or dicarboxylic acid having from 5 to 20 carbon atoms and a coordination complex of organic phosphine and nickel halide, an organic aluminum compound, and hydrogen.

Product olefins such as octenes obtained by the above mentioned dimerization method of lower olefins are hydroformylated and hydrogenated to alcohols having 9 carbon atoms (hereinafter, referred to as "INA"). These alcohols are known to be advantageously used as materials of plasticizers for polyvinyl chloride resin (British Patent No. 789,777and Japanese Patent Publication No. 61-15849, etc.).

As mentioned above, various organic phosphorus compounds have been proposed as ligands used for dimerization reaction. These compounds are, however, not always satisfactory in view of industrial applications. That is, the catalytic systems disclosed in the above ① Japanese Patent Publication No. 46-34007 have faults that they are extremely unstable to air and thus have difficulty to deal with and that synthesis of the catalysis is complex. In addition the catalytic systems disclosed in the above ② Japanese Patent Publication No. 48-30241 involve troublesomeness when used industrially since a complex nickel complex should be synthesized separately.

Dimerization products in the case that reaction material is propylene or butene are obtained normally as a mixture of straight-chain and various branched compounds. In the case that these products may be for the above mentioned alcohol for plasticizers, the lower the degree of branching of the product used is, the higher the reaction rate in hydroformylation is that is useful as a method for synthesizing alcohols for plasticizers, and the lower the degree of branching of resultant alcohol. The alcohol having a lower degree of branching offers higher performance such as heat resistance and cold temperature flexibility, required for alcohols for plasticizers. It is thus an industrial challenge to develop a method of selectively producing dimerized olefins having the lower degree of branching. With this respect, the catalytic systems disclosed in the above ③ Japanese unexamined Patent Publication No. 57-169433 and ④ Japanese Patent Publication No. 3-42249, which are high in dimerization activity, are not suitable for applications in the above mentioned field because the resultant product has a higher ratio of olefin with two branches.

There have been proposed catalytic systems with promoters of various organic phosphorus compounds as the dimerization catalysts for the lower olefin. The existing catalytic systems are not always satisfactory to be used industrially by the considerations of catalyst stability, synthetic methods, catalytic efficiency, and product selectivity and some problems still remain unsolved.

An object of the present invention is to apply the above mentioned dimerized products of the lower olefin to alcohols for plasticizers which are valuable in industrial usage.

The principal aim of the present invention is therefore to develop a dimerization catalyst which is superior in catalytic efficiency and selectivity to a target product, and to develop a method of producing alcohol especially suitable for plasticizers with the resultant dimerization products that has lower degree of branching.

DISCLOSURE OF INVENTION

The present inventors had made tremendous investigation effort to solve the problems in the above mentioned dimerization method of the lower olefin and production of alcohol with the resultant dimerization products. As a result, the inventors have found that (i) a specific dimerization catalyst promotes reaction with an extremely high activity while improving selectivity to the dimerization products and that (ii) the plasticizer performance, in particular the heat resistance and the cold temperature flexibility, is improved when the alcohol for plasticizer is produced with the said dimerization product. The present invention was thus completed.

Namely, the present invention is directed to a method of dimerizing lower olefins which comprises dimerizing a lower olefin in the presence of a catalyst, wherein the catalyst used comprises a nickel compound, an organic aluminum compound, and a phosphite compound having the general formula (I):

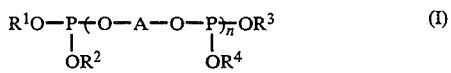

wherein $R^1$, $R^2$, $R^3$ and $R^4$ are phenyl groups optionally substituted by substituents and may be different from each other, at least two of $R^1$, $R^2$, $R^3$, and $R^4$ have a hydrocarbon group as a substituent in the ortho position; A is a divalent aliphatic, alicyclic or aromatic hydrocarbon group which optionally has a substituent; and n is 0 or 1. The present invention is also directed to a method of producing alcohol by means of hydroformylating and hydrogenating the newly formed olefins obtained through the said dimerization method of the lower olefins.

The present invention is described in detail below.

The lower olefins used in the dimerization method according to the present invention include ethylene, propylene, butenes, pentenes, and a mixture thereof. Considering application to the alcohols for plasticizers, propylene, butenes, pentenes, and a mixture thereof are preferable, and specifically butenes are more preferable.

As butenes, butene fraction having a high content of n-butene which is obtained by means of separating butadiene and isobutene from $C_4$ fraction (BB fraction) produced through thermal cracking of hydrocarbon oil such as naphtha, may be used preferably. Further, the BB fraction resulting from catalytic cracking (such as FCC) of hydrocarbon oil such as heavy oil is a mixture of mainly butene and butane, and butene fraction having a high content of n-butene which is obtained by separating isobutene through distillation from the mixture, may also be used preferably.

In dimerization reaction of these butenes, octene of a low degree of branching can be produced with a high activity by using a specific catalytic system according to the present invention. The term "degree of branching" used herein means the number of groups such as methyl group or ethyl groups branched from the hydrocarbon of a main chain. For example, the degrees of branching of n-octene, 3-methylheptene and 3,4-dimethylhexene are 0, 1, and 2, respectively. An average degree of branching of an octene mixture means an average of these values. For example, the average degree of branching is 1.5 for mixed octene containing equal amounts of 3-methylheptene and 3,4-dimethylhexene.

The dimerization catalyst used in the present invention is a catalyst comprising (i) a nickel compound, (ii) an organic aluminum compound, and (iii) a phosphite compound having a general formula (I):

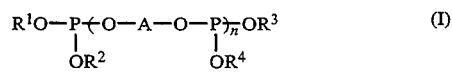

wherein $R^1$, $R^2$, $R^3$, and $R^4$ are phenyl groups optionally substituted by substituents and may be different from each other, at least two of $R^1$, $R^2$, $R^3$, and $R^4$ having hydrocarbon group as a substituent in the ortho position; A is divalent aliphatic hydrocarbon group, alicyclic hydrocarbon group or aromatic hydrocarbon group which optionally has substituents; and n is 0 or 1.

The nickel compound used in the present invention is not limited to a specific one and may be any one of known compounds. Examples of the nickel compound are those available readily such as carboxylic acid salts of nickel such as nickel formate, nickel acetate, nickel octanoate, nickel dodecanate, nickel naphthenate, nickel oleate, and nickel benzoate; complex compounds of nickel such as bis-acetylacetonato-nickel and bis-cyclooctadiene-nickel; and inorganic acid salts of nickel such as nickel chloride, nickel bromide, nickel iodide, nickel nitrate, and nickel sulfate. Of these, carboxylic acid salts of nickel having from 1 to 18 carbon atoms and bis-acetylacetonato-nickel are preferably used.

As the organic aluminum compound, any one of known compounds may be used. For example, trialkylaluminum compounds represented by the general formula $AlR_3$ (wherein R is alkyl group having from 1 to 5 carbon atoms), monohalogeno-dialkylaluminum, dihalogeno-monoalkylaluminum, sesquihalogeno-alkylaluminum compounds represented by the general formula $AlR_2X$, $AlRX_2$, or $Al_2R_3X_3$ (wherein R is alkyl group having from 1 to 5 carbon atoms and X is a halogen atom), and organic aluminoxane compounds in which the above mentioned trialkylaluminum or halogeno-alkylaluminum is partially hydrolated, may be used. Specific examples of the compounds represented by the general formula $AlR_3$ are: trimethylaluminum, triethylaluminum, tri-n-propylaluminum, tri-n-butylaluminum, triisopropylaluminum, triisobutylaluminum, and tri-t-butylaluminum. Specific examples of the compounds represented by the general formula $AlR_2X$, $AlRX_2$, or $A_2R_3X_3$ are: diethylaluminum monochloride, ethylaluminum dichloride, ethylaluminum sesquichloride, propylaluminum dichloride, and isobutylaluminum dichloride. Of these organic aluminum compounds, halogenated alkyl aluminum compounds are preferable, and the dihalogeno-monoalkylaluminum compound such as ethylaluminum dichloride is particularly preferable.

In the present method, it is possible to obtain the dimerized olefin mixture having a low degree of branching with a higher activity as compared with conventional catalysts by means of containing the specific phosphite compound having the general formula (I) in the catalyst system comprising a nickel compound and an organic aluminum compound. The dimerization activity is low when the catalytic components contain no phosphite compound described above or when other phosphite compounds are used such as trialkyl phosphite or triaryl phosphite having no substituent in the ortho position. In addition, the degree of branching of the resultant product is insufficient and the performance of the alcohols for plasticizers is not necessarily satisfactory that are produced using these olefins as the raw material.

The phosphite compound used in the present invention is represented by the above mentioned general formula (I). In $R^1$, $R^2$, $R^3$, and $R^4$ in the above formula, hydrocarbon group of a substituent in phenyl group having hydrocarbon group in the ortho position may be, for example, alkyl group, aralkyl group, aryl group, cycloalkyl group, etc. Of these, alkyl group having from 3 to 20 carbon atoms is preferable, and alkyl group having from 3 to 6 carbon atoms is more preferable. Examples of such alkyl group include isopropyl group, tertiary butyl group, tertiary pentyl group, and tertiary hexyl group. The substituents in other than the ortho position may be, alkoxy group such as methoxy group and ethoxy group, and alkoxycarbonyl group such as methoxycarbonyl group and ethoxycarbonyl group in addition to the above mentioned exemplified substituents in the ortho position. In particular, alkyl group having from 1 to 6 carbon atoms is preferably used.

The number of hydrocarbon groups in the ortho position, or the substituents in $R^1$, $R^2$, $R^3$, and $R^4$, is preferably equal in number to three for n=0, i.e., for a monodentate phosphite compound considering stability and industrial advantages in synthesis, though depending on the type of the substituent. The number is preferably equal to four for n=1, i.e., for a bidentate phosphite compound considering stability and industrial advantages in synthesis, though depending on the type of the substituent.

In the above mentioned general formula (I), when n=1, a group A is typically divalent aliphatic hydrocarbon group having from 2 to 6 carbon atoms (preferably, ethylene group, propylene group, or butylene group), alicyclic hydrocarbon group having from 4 to 12 carbon atoms (preferably cyclohexylene group), or aromatic hydrocarbon group having from 6 to 12 carbon atoms (preferably, phenylene group, biphenylene group, or naphthylene group), which may have substituents such as alkyl group having from 1 to 10 carbon atoms, alkoxy group having from 1 to 5 carbon atoms, phenyl group, and cyclohexyl group (preferably alkyl group, and more preferably alkyl group having from 1 to 6 carbon atoms).

Further the group A is represented by —R— or —R—B— R— wherein R is similar to the above mentioned divalent aliphatic hydrocarbon group, divalent alicyclic hydrocarbon group or divalent aromatic hydrocarbon group, which may have substituents such as alkyl group having from 1 to 10 carbon atoms, alkoxy group having from 1 to 5 carbon atoms, phenyl group, and cyclohexyl group (preferably alkyl group, and more preferably alkyl group having from 1 to 6 carbon atoms); B is selected from the group consisting of —$CR^5R^6$—, —S—, and —O—; $R^5$ and $R^6$ are each selected from the group consisting of a hydrogen atom, and alkyl group having from 1 to 5 carbon atoms.

More specifically, the group A may be, but not limited to, alkylene group such as —$(CH_2)_n$—(n=2-6), —$CH_2CH(CH_3)$—, and —$CH_2$—$C(CH_3)_2CH_2$—, 1,2-cyclobutylene group, 1,2-cyclohexylene group, 1,4-cyclohexylene group, 1,2-phenylene group, 1,4-phenylene group, 2,3-naphthylene group, 1,8-naphthylene group, 2,2'-biphenylene group, 2,2'-methylenebisphenylene group, 4,4'-methylenebisphenylene group, 4,4'-thiobisphenylene group, and 1,2-cyclohexanedimethylene group.

Details have not yet been found about an effect of the phosphite compound having the general formula (I) on the structure or reactivity of the dimerization catalyst. It is, however, expected that the substituents in the ortho positions of at least two of $R^1$, $R^2$, $R^3$, and $R^4$ permit to avoid undesirable reaction with the organic aluminum compound as a Lewis acid, and hence stable and active catalytic structure is maintained.

A method of preparing the phosphite compound having the above general formula (I) is not limited to a specific one. For example, when n=0 in the general formula (I), the phosphite compound can readily be prepared by means of reacting phenol compounds corresponding to $R^1$, $R^2$, and $R^3$ with phosphorus trichloride in a solvent such as toluene in the presence of an amine compound. In this event, $R^1$, $R^2$, and $R^3$ are similar to those defined in the formula (I).

On the other hand, when n=1, the phosphite compound can readily be prepared by means of first reacting phenol compounds corresponding to $R^1$, $R^2$, $R^3$, and $R^4$ with phosphorus trichloride to produce an intermediate $ClP(OR^1)(OR^2)$ or $ClP(OR^3)(OR^4)$ and then reacting the intermediate with a compound represented by the general formula $A(OH)_2$. In this event, $R^1$, $R_2$, $R^3$ and $R^4$, and A are similar to those defined in the formula (I).

Of the above mentioned phenol compound corresponding to $R^1$, $R^2$, $R^3$, and $R^4$, examples of the phenol compound having hydrocarbon group in the ortho position include 2-t-butyl phenol, 2,4-di-t-butyl phenol, 2-isopropyl phenol, 2-t-amyl phenol, 2-t-hexyl phenol, 2,4-di-t-amyl phenol, 6-t-butyl-2,4-xylenol, 3-t-butyl-4-hydroxyanisole, 3-t-butyl-4-hydroxybiphenyl, and 2-t-butyl-p-cresol.

In addition, examples of the above mentioned compound represented by the above general formula $A(OH)_2$ include 2,5-di-t-butyl hydroquinone, 2,5-di-t-amylhydroquinone, 2,5-dimethyl hydroquinone, bisphenol A, 4,4'-methylene bis(2-methyl-6-t-buthyl phenol), 4,4'-butylydene bis(3-methyl-6-t-butyl phenol), 4,4'-thio bis(2-methyl-6-t-buthyl phenol), 2,2'-biphenyldiol, 2,2'-dihydroxydiphenyl methane, 2,2'-methylene bis(4-methyl-6-t-butyl phenol), 2,3-dihydroxynaphthalene, ethylene glycol, 1,3-propanediol, 1,4-butanediol, cis-1,2-cyclohexanediol, and cis-1,2-cyclohexanedimethanol.

Typical examples of the phosphite compound having the general formula (I) used in the present invention are given below.

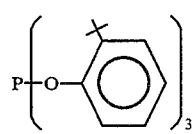 (1)

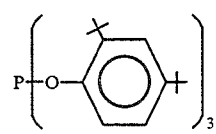 (2)

-continued
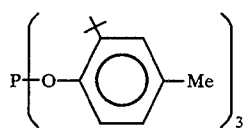 (3)
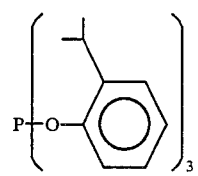 (4)
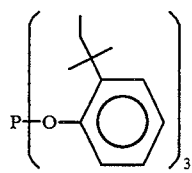 (5)
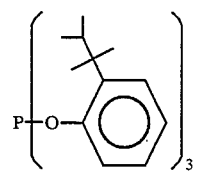 (6)
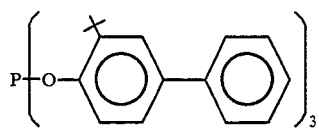 (7)
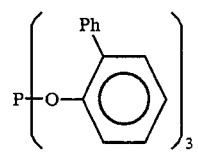 (8)
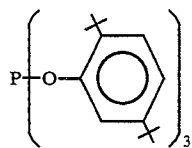 (9)
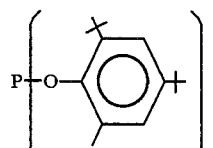 (10)
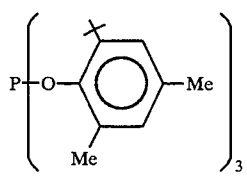 (11)
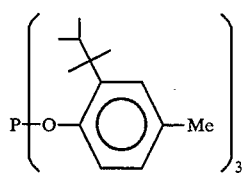 (12)
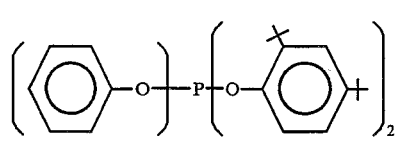 (13)
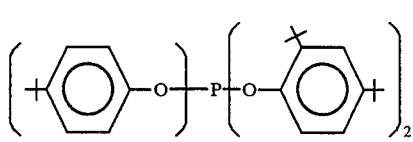 (14)
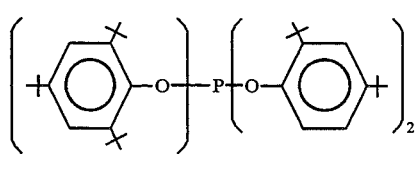 (15)
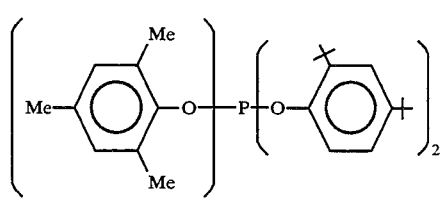 (16)
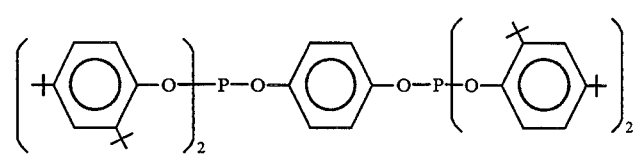 (17)
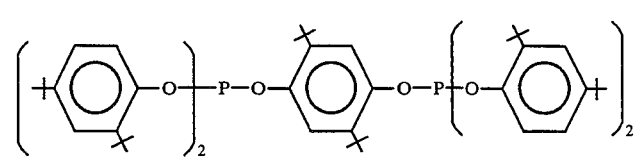 (18)

-continued
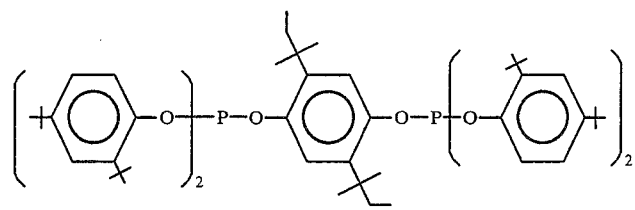
(19)
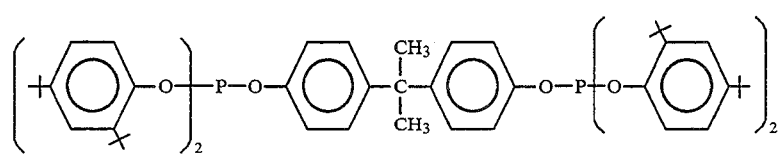
(20)
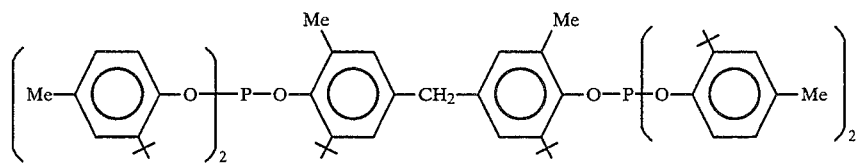
(21)
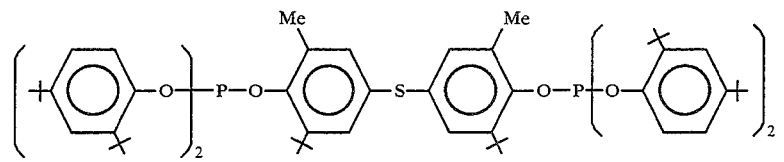
(22)
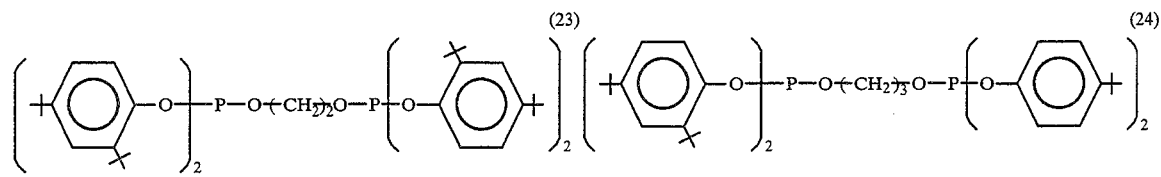
(23) (24)
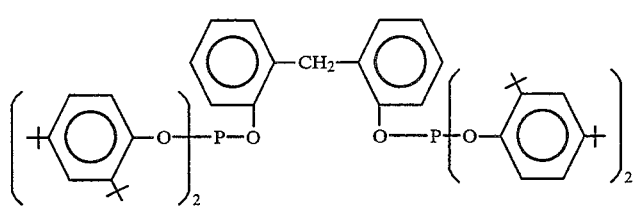
(25)
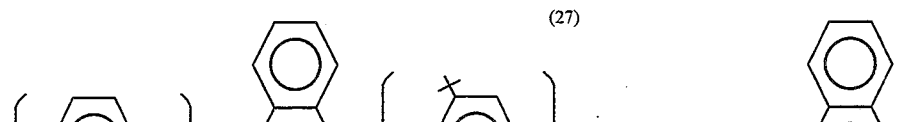
(26)
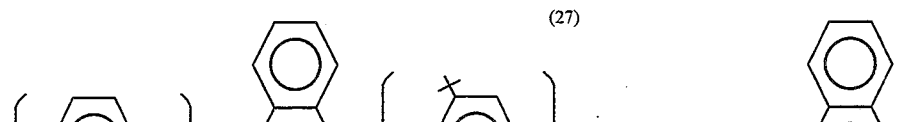
(27) (28)

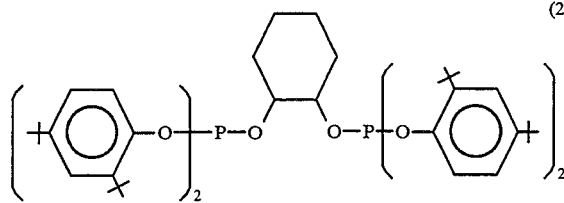

(29)

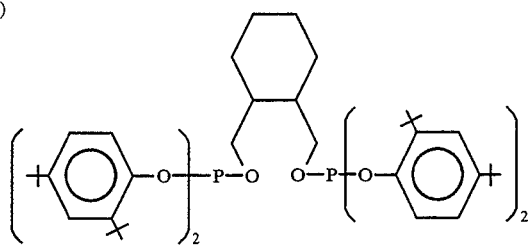

(30)

054457643

Symbols representing substituents in the above structural formulae are as follows.

──╋─ ... tertiary butyl group

──Υ ... isopropyl group

──╋─ ... tertiary amyl group

──╋─ ... tertiary hexyl group

Me ... methyl group

Ph ... phenyl group

In the present method, the catalytic activity can further be improved by containing hydrogen in a reaction system. While the mechanism thereof is not clearly known, various reasons such as removal of impurities in the reaction system (e.g., a reaction inhibitor such as conjugate diene), promoted formation of active form of catalyst and contribution of catalytic stability, etc, are considered. Anyway, coexistence of hydrogen clearly improves the dimerization activity. The amount of hydrogen used is not limited to a specific value and may be in such a range that gives preferable effects on the catalytic activity. Usually, the amount of hydrogen is in the range from 0.01 to 50 kg/cm$^2$, preferably from 0.1 to 20 kg/cm$^2$, based on hydrogen partial pressure.

In dimerization method of lower olefins performed according to the present invention, each catalytic components, i.e., the nickel compound, the phosphite compound having the general formula (I), and the organic aluminum compound, can be mixed in any order. It is, however, preferable to use after forming a mixture or a complex of the nickel compound with the phosphite compound having the general formula (I) previously prepared. In addition, it is preferable for producing a dimerized olefin like octenes having the high activity and low degree of branching to contact these Ni—P compound simultaneously with the organic aluminum compound in the presence of the lower olefin, e.g., butenes.

A reaction solvent may not necessarily used in the method according to the present invention, but an inert solvent, for example, aromatic hydrocarbons such as benzene, toluene, xylene, and dodecylbenzene, aliphatic hydrocarbons such as hexane, heptane, and cyclohexane, and halogenated aromatic hydrocarbons such as chlorobenzene, may be used.

The concentration of the nickel component in a liquid phase in dimerization reaction typically ranges from $10^{-2}$ to $10^2$ mmol/l. A molar ratio of the respective catalytic components affects the dimerization activity and distribution of the resultant products. The molar ratio of the organic aluminum compound to the nickel compound in the catalyst of the present invention is usually in a range from 2 to 100, and preferably from 5 to 50. In addition, the molar ratio of the phosphite compound having the general formula (I) to the nickel compound is usually in the range from 0.1 to 20, and preferably from 1.0 to 5.

An excessively low molar ratio of the organic aluminum compound to the nickel compound in the solvent significantly deteriorates the catalytic activity due to reaction with trace amounts of oxygen or water etc. in dimerization reaction. On the other hand, an unnecessarily high molar ratio less improves the dimerization activity and is not advantageous by the economic considerations. The dimerization activity is deteriorated at an extremely low molar ratio of the above mentioned specific phosphorus compound to the nickel compound, causing the resultant olefin to have high degree of branching. The extremely high molar ratio also deteriorates the dimerization activity, though depending on the amount of the organic aluminum compound, and is not advantageous by the economic considerations.

For dimerization conditions conducted in the present invention, a reaction temperature usually ranges from $-10°$ to $100°$ C., preferably from $0°$ to $80°$ C., and more preferably from $10°$ to $80°$ C. The reaction temperature is properly determined depending on productivity of the process and stability of the nickel and organic aluminum compounds used, etc.

It is effective to let the catalytic components be present sufficiently in a liquid phase of the lower olefins such as butenes and the reaction pressure is preferably in an amount of around 2–30 kg/cm$^2$. Dimerization method according to the present invention may be performed even while paraffin-based hydrocarbons such as methane, ethane, propane, and butane, or inert gases such as nitrogen, argon, and carbon dioxide are contained in the raw materials of the reaction. Dimerization reaction may be performed in either continuous or batch manner.

In the dimerization method of present invention, the selectivity of the resultant product is greatly affected by the reaction conditions, in particular the catalyst concentration, the reaction temperature, the reaction time (contacting time). Generally, the reaction activity is improved by raising the reaction conditions. However, reactivity for trimerization or higher oligomerization is also increased, whereby the selectivity to the desired dimerized olefins decrease. In particular, the contents of normal form and monomethyl form are decrease.

Next, a method of producing alcohols is described in detail that have one more carbon as the newly formed olefin, obtained by using, as the raw material, the newly formed olefin (e.g., octene) obtained through the above mentioned dimerization method of lower olefins (e.g., butenes).

In the method in the present invention, first the newly formed olefin obtained through the above dimerization reaction of lower olefin is usually rectified at a normal or reduced pressure to separate a higher-boiling fraction, etc. which are contained in small amounts. The olefin fraction obtained by the rectification is then hydroformylated by reaction with carbon monoxide and hydrogen to produce aldehyde having one more carbon as the produced olefin.

The above hydroformylation reaction is performed according to a conventional method. The reaction conditions of the hydroformylation are not particularly critical and either a conventional rhodium or cobalt method, may be used.

As a rhodium source in the case of the rhodium method, organic salts such as $Rh(OAc)_3$; inorganic salts such as $Rh(NO_3)_3$, and $RhCl_3$; and complexes such as $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$, may be used.

As a cobalt source in the case of the cobalt method, in addition to organic salts such as cobalt laurate and inorganic salts such as $Rh(NO_3)_3$, complexes such as $Co_2(CO)_8$ and $CoH(CO)_4$ may be used The conditions usually used are: the reaction pressure of from normal pressure to 300 $kg/cm^2G$; the reaction temperature of 50°–150° C.; the $H_2/CO$ ratio of 1–10 by molar ratio; and the catalyst concentration of 0.1–1000 ppm (Rh atom). As a ligand, the organic phosphorus compounds such as triphenyl phosphine and triphenyl phosphite, or oxides thereof may suitably be used usually at molar ratio from 1 to 1000 to the above catalyst.

The reaction solvent is not necessary. A solvent inert to the reaction, for example, aromatic hydrocarbons such as benzene, toluene, xylene, and dodecylbenzene; aliphatic hydrocarbons such as hexane, heptane, and cyclohexane; ethers such as dibutyl ether, ethylene glycol dimethyl ether, triethylene glycol dimethylether, and tetrahydrofuran; and esters such as diethyl phthalate, and dioctyl phthalate, may be used depending on necessity. In addition, aldehydes and alcohols formed through hydroformylation reaction may also be used as the solvent. Alternatively, higher-boiling by-products such as polycondensation products of aldehyde may be also used. The reaction may be performed in an either continuous or batch manner.

In the above hydroformylation reaction, the structure of the resultant aldehyde varies significantly depending on the central metal of the catalyst used as well as the ligands. Namely, in general, with the rhodium catalyst, the hydroformylation activity is by far higher than with the cobalt one but the hydroformylation with the rhodium catalyst yields more branched aldehyde due to its strong internal isomerization ability. Because the above mentioned octenes used in the present invention have low degree of branching, it has advantages that even if the hydroformylation reaction is conducted by a rhodium method, the alcohols finally obtained will have relatively low degrees of branching, and that the hydroformylation activity will increase.

The resultant aldehydes is hydrogenated to alcohols. This may be performed according to a conventional method. Namely, the aldehyde is hydrogenated using a conventional catalyst such as Ni, Cr, or Cu at the reaction pressure usually of from normal pressure to 150 $kg/cm^2G$, and the reaction temperature usually of from 40° to 300° C. Then alcohols can be obtained by a conventional rectification.

The alcohol so obtained, in particular the alcohols having 9 atoms (INA) produced with the butene as raw material, may be esterified with an acid such as phthalic anhydride or adipic acid through a conventional method and then purified into plasticizer (e.g., phthalate plasticizer). The resultant plasticizer exhibits good performances.

BEST MODE FOR CARRYING OUT THE INVENTION

The foregoing features of the present invention will be more readily apparent in the context of a specifically delineated set of examples and a reference. However, it should be understood that the present invention is not limited to those particular examples and the reference as long as not being depart from the spirit and scope of the appended claims.

EXAMPLE 1

A stainless steel micro-autoclave having an internal capacity of 70 ml was deaerated and subjected to substitution with nitrogen. An m-xylene solution containing 8.28 mg of nickel octanoate, and 3 moles of tris(2-t-butyl phenyl)phosphite per 1 mole of a nickel atom (P/Ni=3) was loaded into the micro-autoclave along with a pentane solution containing 38.1 mg of ethylaluminum dichloride (Al/Ni=12.5) under a nitrogen atmosphere. Subsequently, 20 ml of trans-2-butene was loaded into the micro-autoclave. This micro-autoclave was sealed and the reaction was conducted at 40° C. for 5 hours under stirring. After completion of the reaction, the micro-autoclave was cooled to a room temperature and purged of non-reacted gases, to which 2 ml of methanol was added to stop the reaction.

The reaction solution was analyzed on product concentration through gas chromatography (column: CBP1 capillary of 0.25 $\phi \times 50$ m manufactured by Shimadzu Corporation and 10% SE-30/Chromosorb 2 m).

The results are set forth in Table 1.

COMPARATIVE EXAMPLE 1

A dimerization reaction of trans-2-butene was conducted in the same manner as in Example 1 except that no phosphite compound was added.

The results of reaction are set forth in Table 1.

COMPARATIVE EXAMPLES 2 and 3

Dimerization reactions of trans-2-butene were conducted in the same manner as in Example 1 except that triphenyl phosphite and triethyl phosphite were used, respectively, 3 moles for each per 1 mole of a nickel atom (P/Ni=3) in place of tris(2-t-butyl phenyl)phosphite.

The results of reaction are set forth in Table 1.

EXAMPLES 2 through 9

Dimerization reactions of trans-2-butene were conducted in the same manner as in Example 1 except that various phosphite compounds set forth in Table 1, at an amount of 3 moles of phosphorus atoms per 1 mole of a nickel atom (P/Ni=3), were used in place of tris(2-t-butyl phenyl)phosphite.

The results of reaction are set forth in Table 1.

EXAMPLE 10

A dimerization reaction of trans-2-butene was conducted in the same manner as in Example 1 except that 3.19 mg of his(acetyl acetonato)nickel was used in place of nickel octanoate and that 3 moles of tris(2,4-di-t-butyl phenyl)phosphite per 1 mole of a nickel atom (P/Ni=3) was used in place of tris(2-t-butyl phenyl)phosphite.

The results of reaction are set forth in Table 1.

EXAMPLE 11

A dimerization reaction of trans-2-butene was conducted in the same manner as in Example 1 except that a hydrogen gas was injected up to a total pressure of 5 kg/cm$^2$.G after trans-2-butene was loaded.

The results of reaction are set forth in Table 1.

COMPARATIVE EXAMPLE 4

A dimerization reaction of trans-2-butene was conducted in the same manner as in Example 11 except that no phosphite compound was added.

The results of reaction are set forth in Table 1.

COMPARATIVE EXAMPLE 5 and 6

Dimerization reactions of trans-2-butene were conducted in the same manner as in Example 11 except that triphenyl phosphite and triethyl phosphite were used, respectively, 3 moles for each per 1 mole of a nickel atom (P/Ni=3) in place of tris(2-t-butyl phenyl)phosphite.

The results of reaction are set forth in Table 1.

EXAMPLE 12 through 19

Dimerization reactions of trans-2-butene were conducted in the same manner as in Example 11 except that various phosphite compounds set forth in Table 1, at an amount of 3 moles for each per 1 mole of a nickel atom (P/Ni=3), were used in place of tris(2-t-butyl phenyl)-phosphite.

The results of reaction are set forth in Table 1.

EXAMPLE 20

A dimerization reaction of trans-2-butene was conducted in the same manner as in Example 11 except that nickel octanoate was replaced by 3.33 mg of bis(1,5-cyclooctadiene)nickel (0), and that 3 moles of tris(2-t-butyl phenyl)phosphite per 1 mole of a nickel atom (P/Ni= 3), and 19.05 mg of ethylaluminum dichloride (Al/Ni=12.5) were used and 20 ml of trans-2-butene was stirred at 40° C. for 2 hours under hydrogen pressure of 5 kg/cm$^2$.G.

The results of reaction are set forth in Table 1.

EXAMPLE 21 and Comparative Example 7

Dimerization reactions of trans-2-butene were conducted in the same manner as in Example 20 except that phosphite compounds set forth in Table 1 were used at an amount of 3 moles per 1 mole of a nickel atom (P/Ni=3) in place of tris(2-t-butyl phenyl)phosphite.

The results of reaction are set forth in Table 1.

TABLE 1

| CASE No. | Phosphite Compound | Oligomer Yield *1 (%) | | | C$_8$ Olefin Skeleton Distribution *2 (%) | | | Average Degree of Branching |
|---|---|---|---|---|---|---|---|---|
| | | C$_8$ Olefin | C$_{12}$ Olefin | C$_{16}$ Olefin | n-Octene | 3-methyl-heptene | 3,4-di-methyl-hexene | |
| Example 1 | P—(O—⟨⟩—⧫)$_3$ | 65.1 | 3.7 | trace | 6.0 | 78.5 | 15.5 | 1.10 |
| Comparative Example 1 | — | 29.3 | 1.0 | 0.3 | 5.1 | 63.8 | 31.0 | 1.26 |
| Comparative Example 2 | P—(O—⟨⟩)$_3$ | 14.1 | trace | 0 | 3.6 | 70.7 | 25.8 | 1.22 |
| Comparative Example 3 | P—(OEt)$_3$ | 5.4 | 2.0 | trace | 7.9 | 64.4 | 27.6 | 1.20 |
| Example 2 | P—(O—⟨⟩+—⧫)$_3$ | 61.9 | 3.2 | trace | 6.0 | 80.6 | 13.4 | 1.07 |
| Example 3 | P—(O—⟨⟩—⧫)$_3$ | 65.8 | 3.6 | trace | 6.2 | 78.5 | 15.3 | 1.09 |
| Example 4 | P—(O—⟨⟩)$_3$ | 64.2 | 3.7 | trace | 5.9 | 78.6 | 15.5 | 1.10 |
| Example 5 | P—(O—⟨⟩)$_3$ | 63.0 | 3.6 | trace | 6.3 | 78.3 | 15.4 | 1.09 |

TABLE 1-continued

| CASE No. | Phosphite Compound | Oligomer Yield *1 (%) | | | C8 Olefin Skeleton Distribution *2 (%) | | | Average Degree of Branching |
|---|---|---|---|---|---|---|---|---|
| | | C8 Olefin | C12 Olefin | C16 Olefin | n-Octene | 3-methyl-heptene | 3,4-di-methyl-hexene | |
| Example 6 | 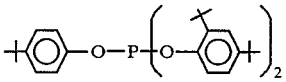 | 69.4 | 3.8 | trace | 5.6 | 79.2 | 15.2 | 1.10 |
| Example 7 | 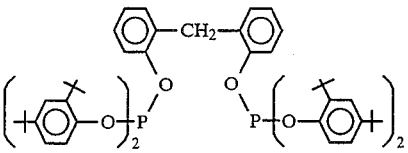 | 70.0 | 4.1 | trace | 5.2 | 77.2 | 17.6 | 1.12 |
| Example 8 | 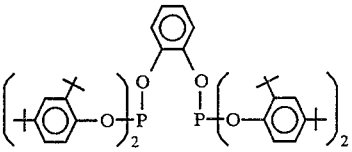 | 67.8 | 3.7 | trace | 5.7 | 78.2 | 16.1 | 1.10 |
| Example 9 | 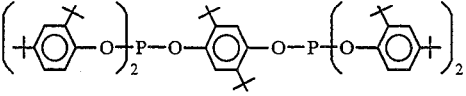 | 50.5 | 1.8 | 0 | 5.7 | 77.4 | 16.8 | 1.11 |
| Example 10 | 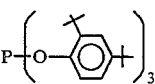 | 59.3 | 2.7 | 0 | 6.1 | 79.6 | 14.3 | 1.08 |
| Example 11 | 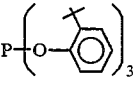 | 84.1 | 12.8 | 1.7 | 5.0 | 79.3 | 15.7 | 1.11 |
| Comparative Example 4 | — | 28.2 | 0.9 | trace | 9 | 61 | 30 | 1.21 |
| Comparative Example 5 | 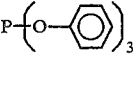 | 18.4 | trace | trace | 4 | 71 | 25 | 1.21 |
| Comparative Example 6 | P(OEt)$_3$ | 8.4 | 2.1 | trace | 8 | 64 | 28 | 1.20 |
| Example 12 | 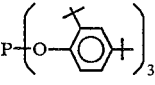 | 85.0 | 12.9 | 1.7 | 6 | 79 | 15 | 1.09 |
| Example 13 | 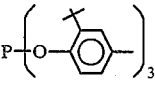 | 84.5 | 12.1 | 1.4 | 6 | 79 | 15 | 1.09 |
| Example 14 | 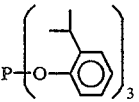 | 84.0 | 11.7 | 1.2 | 6 | 78 | 16 | 1.10 |
| Example 15 | 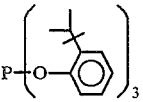 | 82.5 | 10.1 | 1.2 | 6 | 78 | 16 | 1.10 |

TABLE 1-continued

| CASE No. | Phosphite Compound | Oligomer Yield *1 (%) | | | C8 Olefin Skeleton Distribution *2 (%) | | | Average Degree of Branching |
|---|---|---|---|---|---|---|---|---|
| | | $C_8$ Olefin | $C_{12}$ Olefin | $C_{16}$ Olefin | n-Octene | 3-methyl-heptene | 3,4-di-methyl-hexene | |
| Example 16 | | 85.5 | 12.5 | 2.0 | 5 | 78 | 17 | 1.12 |
| Example 17 | | 85.2 | 12.3 | 1.6 | 5 | 77 | 18 | 1.13 |
| Example 18 | | 83.4 | 11.6 | 1.5 | 6 | 78 | 16 | 1.10 |
| Example 19 | | 75.0 | 7.9 | 0.7 | 5 | 79 | 16 | 1.11 |
| Example 20 | | 78.0 | 7.4 | 0.5 | 5 | 78 | 17 | 1.12 |
| Example 21 | | 70.5 | 5.5 | 0.3 | 5 | 78 | 17 | 1.12 |
| Comparative Example 7 | | 41.9 | 1.4 | trace | 4 | 72 | 24 | 1.20 |

*1) Percent by weight of newly formed oligomer to loaded butene
*2) Percent by mole of each skeletal isomer to all octene produced

EXAMPLE 22

(1) Synthesis of Octenes 1.71 kg of trans-2-butene which was sufficiently dehydrated with molecular sieves 13X and a n-heptane solution of ethylaluminum dichloride (25.45 mmol) were loaded into an induction stirring autoclave made of SUS having an internal capacity of 5 liters under a nitrogen atmosphere. Subsequently, a xylene solution of nickel octanoate (2.05 mmol) and a xylene solution of tris(2,4-di-t-butyl phenyl)phosphite (6.15 mmol), which had previously been loaded in catalyst vessels connected to the autoclave, were introduced into the autoclave under pressure with hydrogen to start reaction with the autoclave being stirred. The reaction was conducted at 45° C. and a total pressure of 7.5 kg/cm²G for 3 hours. After the reaction, the catalyst was inactivated by treatment with a 10%-sulfuric acid solution and then an organic phase was separated. A part of the organic phase was hydrogenated with a 5%-Pd/C catalyst. Skeleton structures of the resultant octenes were analyzed through gas chromatography. The results thereof are set forth below.

| | |
|---|---|
| n-octene | 7% |
| 3-methylheptene | 80% |
| 3,4-dimethylhexene | 13% |
| average degree of branching | 1.06 |

(2) Collection of Octene Fraction through Distillation

The dimerization solution obtained in the above (1) was rectified at a normal pressure by using an Oldershaw column of 30 mm in inner diameter×5 plates. Lower-boiling solvent, higher-boiling fragment, and catalytic components were separated to obtain an octene fraction at from an overhead temperature to 127° C.

(3) Synthesis of Alcohols 600 ml of the octene fraction obtained in the above (2) and 3.50 g of $Co_2(CO)_8$ were introduced under a nitrogen atmosphere into an induction stirring autoclave made of SUS having an internal capacity of 1 liter. The reaction was conducted at 130° C. while the total pressure was maintained at 150 kg/cm$^2$G by an oxo gas of H$_2$/CO=1.

No gas was absorbed after 8 hours, so that the reactor was cooled at a room temperature. A 3%-NaOH aqueous solution was introduced to inactivate the cobalt catalyst, following which the reactor was further cooled. The oxo gas was released and the total amount of the reaction solution was then picked. The solution was subjected to liquid-liquid separation to obtain an organic phase. Subsequently, aldehydes and alcohols were obtained through vacuum simple distillation at a pressure of 10 mmHg.

600 ml of the solution recovered through the above mentioned simple distillation and 60 g of solid catalyst carrying nickel-chromium were loaded in an induction stirring autoclave made of SUS having the internal capacity of 1 liter. The reaction was conducted at a reaction temperature of 150° C. while the total pressure was maintained at 1100 kg/cm$^2$G. Four hours later, gas absorption was stopped and thus the autoclave was cooled to release the hydrogen gas, following which the total amount of the reaction solution was picked up. After the solid catalyst was removed by filteration, the filtrated solution was rectified by using the Oldershaw column of 30 mm in inner diameter×5 plates.

(4) Synthesis of Plasticizers and Evaluations

INA obtained in the above (3) was esterified with phthalic anhydride into plasticizer according to a conventional method. Next, the plasticizer was mixed with vinyl chloride resin at an amount (weight ratio) of 67/100 to produce a plasticized vinyl chloride resin according to a conventional method. The plasticized vinyl chloride resin was subjected to various tests. The results thereof are set forth in Table 2.

Comparative Example 8

Synthesis and evaluation of a plasticizer were conducted in the same manner as Example 22 except that the phosphite compound was not used as the dimerization catalyst of trans-2-butene in synthesis of the octenes, and that reaction was carried out with nickel octanoate-ethylaluminum dichloride-hydrogen catalyst system at 45° C. for 5 hours. The results are set forth in Table 2.

Analysis was made on the hydrogenated skeleton structures of the octenes obtained through the above mentioned dimerization reaction. The results are given below.

| n-octene | 9% |
| 3-methylheptene | 60% |
| 3,4-dimethylhexene | 31% |
| average degree of branching | 1.22 |

COMPARATIVE EXAMPLE 9

Synthesis and evaluation of a plasticizer were conducted in the same manner as Example 22 except that triphenyl phosphite was used as the phosphite compound of the dimerization catalyst of trans-2-butene in place of tris(2,4-di-t-butyl phenyl)phosphite in synthesis of the octenes. The results are set forth in Table 2.

Analysis was made on the hydrogenated skeleton structures of the octenes obtained through the above mentioned dimerization reaction. The results are given below.

| n-octene | 4% |
| 3-methylheptene | 70% |
| 3,4-dimethylhexene | 26% |
| average degree of branching | 1.22 |

|  | Example 22 | Comparative Example 8 | Comparative Example 9 |
|---|---|---|---|
| Plasticizing Efficiency [100% modulus] (kg/cm$^2$) | 76 | 78 | 77 |
| Volatile Loss [120° C. × 5 days] | 14.2 | 14.9 | 15.0 |
| Cold Flex Temperature (°C.) | −38.2 | −36.6 | −36.7 |
| Kerosene Extraction (%) [room temperature; one day] | 42.4 | 41.8 | 41.0 |
| Electrical Resistance [×10$^{13}$ Ω · cm] | 2.3 | 2.5 | 2.4 |

INDUSTRIAL APPLICABILITY

In the dimerization method of the lower olefins according to the present invention, it is possible to produce in an economic manner olefinic mixtures which are high in activity and low in degree of branching. In addition, the alcohols produced with the said olefins show totally superior performance as the raw material for plasticizers, which are thus valuable in industrial applications.

We claim:

1. A method of dimerizing lower olefins which comprises dimerizing a lower olefin in the presence of a catalyst, wherein the catalyst used comprises a nickel compound, an organic aluminum compound, and a phosphite compound having the general formula (I):

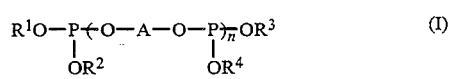

wherein R$^1$, R$^2$, R$^3$, and R$^4$ are phenyl groups optionally substituted by substituents and may be different from each other, at least two of R$^1$, R$^2$, R$^3$, and R$^4$ have a hydrocarbon group as a substituent in the ortho position; A is a divalent aliphatic, alicyclic or aromatic hydrocarbon group which optionally has a substituent; and n is 0 or 1.

2. A method as claimed in claim 1, wherein the lower olefin is a butene.

3. A method as claimed in claim 1, wherein the nickel compound is a nickel carboxylate.

4. A method as claimed in claim 1, wherein the nickel compound is a complex compound of nickel.

5. A method as claimed in claim 1, wherein the organic aluminum compound is a halogenated alkylaluminum compound.

6. A method as claimed in claim 1, wherein the hydrocarbon groups which at least two of R$^1$, R$^2$, R$^3$, and R$^4$ in the phosphite compound having the general formula (I) have as a substituent in the ortho position, are alkyl groups.

7. A method as claimed in claim 1, wherein n in the phosphite compound having the general formula (I) is equal to zero.

8. A method as claimed in claim 7, wherein all of $R^1$, $R^2$, and $R^3$ in the phosphite compound having the general formula (I) have a hydrocarbon group as the substituent in the ortho position.

9. A method as claimed in claim 1, wherein n in the phosphite compound having the general formula (I) is equal to one.

10. A method as claimed in claim 9, wherein all of $R^1$, $R^2$, $R^3$, and $R^4$ in the phosphite compound having the general formula (I) have a hydrocarbon group as the substituent in the ortho position.

11. A method as claimed in claim 9, wherein the group A in the phosphite compound having the general formula (I) is a divalent aliphatic hydrocarbon group having from 2 to carbon atoms.

12. A method as claimed in claim 9, wherein the group A in the phosphite compound having the general formula (I) is an alicyclic hydrocarbon group having from 4 to 12 carbon atoms.

13. A method as claimed in claim 9, wherein the group A in the phosphite compound having the general formula (I) is an aromatic hydrocarbon group having from 6 to 12 carbon atoms.

14. A method as claimed in claim 9, wherein the group A in the phosphite compound having the general formula (I) is represented by —R—B—R— wherein R is a divalent aliphatic hydrocarbon group, a divalent alicyclic hydrocarbon group or a divalent aromatic hydrocarbon group, which is optionally substituted by an alkyl group having from 1 to 10 carbon atoms, an alkoxy group having from 1 to 5 carbon atoms, phenyl group, or cyclohexyl group; B is selected from the group consisting of —$CR^5R^6$—, —S—, and —O—; $R^5$ and $R^6$ are each selected from the group consisting of a hydrogen atom, and an alkyl group having from 1 to 5 carbon atoms.

15. A method as claimed in claim 1, wherein hydrogen is present in the reaction system.

16. A method of producing alcohols which comprises:

dimerizing a lower olefin in the presence of a catalyst comprising a nickel compound, an organic aluminum compound, and a phosphite compound having the general formula (I):

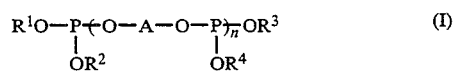

wherein $R^1$, $R^2$, $R^3$, and $R^4$ are phenyl groups optionally substituted by substituents and may be different from each other, at least two of $R^1$, $R^2$, $R^3$, and $R^4$ have a hydrocarbon group as a substituent in the ortho position; A is a divalent aliphatic, alicyclic or aromatic hydrocarbon group which optionally has a substituent; and n is 0 or 1; to obtain dimerized olefins and, subjecting the dimerized olefins to a hydroformylation reaction and a hydrogenation reaction.

17. A method as claimed in claim 16, wherein a rhodium catalyst is used in the hydroformylation reaction.

18. A method as claimed in claim 16, wherein a cobalt catalyst is used in the hydroformylation reaction.

* * * * *

UNITED STATES PATENT AND TRADEMARK OFFICE
CERTIFICATE OF CORRECTION

PATENT NO. : 5,446,213
DATED : August 29, 1995
INVENTOR(S) : Keiichi SATO, et al.

It is certified that error appears in the above-indentified patent and that said Letters Patent is hereby corrected as shown below:

On the title page, Item [30], the Foreign Application Priority Date should read:

--Oct. 6, 1992--

Signed and Sealed this

Fifth Day of December, 1995

Attest:

BRUCE LEHMAN

*Attesting Officer*    Commissioner of Patents and Trademarks